US012758715B2

(12) United States Patent
Carrel

(10) Patent No.: US 12,758,715 B2
(45) Date of Patent: Oct. 13, 2026

(54) AUTOINJECTOR FOR AUTOMATIC INJECTION OF A PRODUCT INTO AN INJECTION SITE

(71) Applicant: Becton Dickinson France, Le Pont-de-Claix (FR)

(72) Inventor: Franck Carrel, Saint Jean de Vaulx (FR)

(73) Assignee: Becton Dickinson France, Le Pont-de-Claix (FR)

( * ) Notice: Subject to any disclaimer, the term of this patent is extended or adjusted under 35 U.S.C. 154(b) by 358 days.

(21) Appl. No.: 18/625,637

(22) Filed: Apr. 3, 2024

(65) Prior Publication Data

US 2024/0335613 A1 Oct. 10, 2024

(30) Foreign Application Priority Data

Apr. 4, 2023 (EP) .................................... 23305489

(51) Int. Cl.

*A61M 5/315* (2006.01)
*A61M 5/20* (2006.01)
*A61M 5/32* (2006.01)

(52) U.S. Cl.

CPC ...... *A61M 5/31501* (2013.01); *A61M 5/2033* (2013.01); *A61M 5/31571* (2013.01);
(Continued)

(58) Field of Classification Search

CPC ............ A61M 5/31501; A61M 5/2033; A61M 5/31571; A61M 5/31578; A61M 5/3202; A61M 5/3234

See application file for complete search history.

(56) References Cited

U.S. PATENT DOCUMENTS

2010/0152659 A1* 6/2010 Streit .................. A61M 5/2033 604/192
2018/0185582 A1* 7/2018 Mikkelsen .......... A61M 5/2033
2020/0353170 A1 11/2020 Atterbury et al.

FOREIGN PATENT DOCUMENTS

GB 2477487 A 8/2011

* cited by examiner

*Primary Examiner* — Dung T Ulsh
(74) *Attorney, Agent, or Firm* — The Webb Law Firm

(57) ABSTRACT

The autoinjector includes a housing extending along a longitudinal axis A and configured to receive a medical container having a barrel defining a reservoir for containing a medical product. The barrel having a distal end provided with an injection needle and an opened proximal end configured to receive a plunger rod for pushing a stopper arranged inside the barrel. A needle cover is coupled to and axially movable with respect to said housing between a first extended position, a retracted position, and a second extended position. A plunger rod is axially movable inside the housing between a storage position and an injection end position, the plunger rod being configured to push the stopper in order to expel the medical product. The autoinjector also includes biasing means for biasing the plunger rod in a distal direction towards the injection end position, a retainer for maintaining the plunger rod in the initial position against the action of the biasing means, the retainer including a blocking member radially movable between a blocking position for blocking the plunger rod in the initial position, and a release position allowing for movement of the plunger rod in the distal direction. A first locker is axially movable with respect to the retainer between a locking position for maintaining the blocking member in the blocking position, and a release position, axial movement of the first locker from the locking position to the release position being caused by the needle cover moving from the first
(Continued)

extended position to the retracted position. A second locker, is rotationally movable around the longitudinal axis A with respect to said housing, between a locking position for preventing axial movement of the first locker from the locking position to the release position, and a release position for allowing axial movement of the first locker from the locking position to the release position. The autoinjector further includes axial securing means for axially securing the second locker with respect to the housing.

15 Claims, 16 Drawing Sheets

(52) U.S. Cl.
CPC ...... *A61M 5/31578* (2013.01); *A61M 5/3202* (2013.01); *A61M 5/3234* (2013.01); *A61M 2005/2013* (2013.01); *A61M 2005/206* (2013.01); *A61M 2005/208* (2013.01)

AUTOINJECTOR FOR AUTOMATIC INJECTION OF A PRODUCT INTO AN INJECTION SITE

CROSS-REFERENCE TO RELATED APPLICATION

This application claims priority to European Patent Application No. 23305489.9 filed Apr. 4, 2023, the disclosure of which is hereby incorporated by reference in its entirety.

BACKGROUND OF THE INVENTION

Field of the Invention

The present invention relates to an autoinjector.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction away from the user's hand, and the "proximal direction" is to be understood as meaning the direction toward the user's hand.

Description of Related Art

Automatic injection devices are designed for automatic injection of a medical product into an injection site. Autoinjectors usually comprise a housing for receiving a medical container. The medical container has a barrel defining a reservoir for containing the medical product, the barrel having a distal end provided with an injection needle and an opened proximal end receiving a plunger rod for pushing a stopper. The opened proximal end is usually provided with a flange.

Autoinjectors also include a safety shield mechanism moving from an extended to a retracted position to respectively shield or unveil the needle and an injection mechanism for automatically injecting the medical product into an injection site. The injection mechanism usually includes a plunger rod for pushing a stopper inside the barrel of the medical container, and an initially compressed spring for moving the plunger rod in the distal direction. Locking means are provided for maintaining the plunger rod in an initial position in which the plunger rod is axially blocked despite the action of the compressed spring. A release member is typically arranged to release the plunger rod from the locking means and allow the spring to push the plunger rod in the distal direction to perform injection. A predetermined displacement of the safety shield towards the retracted position is required to allow the release member to unlock the locking means and release the plunger rod.

To assess the robustness of the autoinjectors, autoinjectors are subjected to drop tests as required in ISO11608. These drop tests usually consist in dropping the autoinjectors at least once from a height of 1 m onto a horizontal floor. There are three drop directions: a drop "cap upward", a drop "cap downward", and a drop with the autoinjector being horizontal. The autoinjectors may be sensitive to the drop test "cap upward".

There is therefore a need for an autoinjector that reduces the risks of being activated during a drop test "cap upward" or any other drop.

To prevent inadvertent activation of an autoinjector during a drop test or an accidental fall of this autoinjector, it is known to use hard dots, in the form of protrusions, that prevent inadvertent movement of the safety shield towards the retracted position. To activate the autoinjectors, the user has to press the autoinjector against an injection site. The force exerted by the user has to overcome a predetermined activation force to force the safety shield to pass over the hard dots and reach the retracted position so that the autoinjector gets activated and the injection is triggered. However, this activation force may sometimes be quite high for the end user who needs healthcare.

There is therefore a need to make the activation force as low as possible, while still preventing inadvertent activation of the autoinjector if the autoinjector drops.

SUMMARY OF THE INVENTION

An aspect of the invention is an autoinjector, for automatic injection of a product into an injection site, said autoinjector comprising:

- a housing extending along a longitudinal axis A and configured to receive a medical container having a barrel defining a reservoir for containing a medical product, said barrel having a distal end provided with an injection needle and an opened proximal end configured to receive a plunger rod for pushing a stopper arranged inside the barrel,
- a needle cover coupled to and axially movable with respect to said housing between a first extended position, in which the needle cover at least partially shields the injection needle, a retracted position, in which the needle cover moves proximally with respect to the housing, and a second extended position in which the needle cover moves back in the distal direction to shield the injection needle,
- a plunger rod axially movable inside the housing between a storage position and an injection end position distally located relative to the storage position, the plunger rod being configured to push the stopper in order to expel the medical product when moving from the storage position to the injection end position,
- biasing means for biasing the plunger rod in a distal direction towards the injection end position,
- a retainer for maintaining the plunger rod in the initial position against the action of the biasing means, the retainer including a blocking member radially movable between a blocking position, in which the blocking member axially abuts against a distal abutment surface of the plunger rod for blocking the plunger rod in the initial position, and a release position, in which the blocking member is away from the distal abutment surface of the plunger rod to allow for movement of the plunger rod in the distal direction,
- a first locker, axially movable with respect to the retainer between a locking position, in which a lateral abutment surface of the first locker radially abuts against the blocking member to maintain the blocking member in the blocking position, and a release position, in which the lateral abutment surface of the first locker is axially shifted away from the blocking member, axial movement of the first locker from the locking position to the release position being caused by the needle cover moving from the first extended position to the retracted position,
- a second locker, rotationally movable around the longitudinal axis A with respect to said housing, between a locking position in which a distal abutment surface of the second locker is configured for axially abutting against a proximal abutment surface of the first locker, thereby preventing axial movement of the locker from the locking position to the release position, and a release position in which the distal abutment surface of the second locker is shifted away from the proximal abutment surface of the first locker, thereby allowing axial movement of the first locker from the locking position to the release position, axial securing means for axially securing the second locker with respect to the housing.

The autoinjector of the invention thus prevents inadvertent activation of the injection mechanism because the second locker prevents the first locker to release the retainer that keeps the plunger rod in the storage position. Meanwhile, the autoinjector of the invention reduces the activation force since it is no longer required to provide the autoinjector with protrusions for hindering any inadvertent axial movement of the first locker towards the release position. The axial abutment between the second locker and the housing is indeed strong enough to prevent such inadvertent axial movement of the first locker.

The autoinjector of the invention may further include some or all of the features below.

In an embodiment, the second locker is arranged at a proximal end of the housing and defines an inner cavity configured for receiving the first locker when the first locker moves from the locking position to the release position. The second locker may be in the form of a top cap configured for closing a proximal opening of the housing. When the autoinjector falls, the second locker hits the floor. The reaction force of the floor exerted upon the second locker increases the resistance of the second locker to the proximal movement of the first locker.

In an embodiment, the biasing means have a proximal end abutting against a distal shoulder of the retainer and an opposite distal end abutting against the plunger rod, and the blocking member includes an inner radial protrusion for engaging a groove of the plunger rod, the inner radial protrusion being arranged proximal to the distal shoulder of the retainer. The inner radial protrusion thus cannot interfere with the biasing means, which may be arranged around the plunger rod. The inner radial protrusion is kept away from the biaising means and cannot rub against said biaising means. This avoids to produce noise due to the coils of the biaising means passing over the inner radial protrusion when the biaising means expand from a compressed state to an extended state.

In an embodiment, the axial securing means include a distal stop arranged on the housing for abutting against a proximal stop of the second locker. The second locker is therefore blocked in the proximal direction by abutment against the housing. Due to the (direct) abutment between the second locker and the housing, the force applied to the second locker by the first locker inadvertently moving towards the release position is transferred to the housing. This reliably prevents inadvertent activation of the autoinjector during drop tests.

In an embodiment, the proximal stop is provided on a radially inwardly deformable circumferential arm of the second locker, and the distal stop is provided on a lug of the housing. Thus, the lug axially blocks a proximal movement of the second locker with respect to the housing.

In an embodiment, the second locker further includes two axial arms for connecting the circumferential arm to the second locker, the two axial arms and the circumferential arm defining a window configured for receiving the lug. The window and the lug form snap-fitting means for securing the second locker to the housing. The two axial arms increase the resistance of the circumferential arm and so the resistance of the second locker against inadvertent proximal movements of the first locker. The axial arms and the circumferential arm are configured to (inwardly) flex so that they can pass over the lug when the second locker is assembled to the housing. The lug may include a proximal ramp portion for easing inward deformation of the circumferential arm and axial arms when the second locker is assembled to the housing.

Possibly, the second locker includes axial slots extending adjacent the axial arms. The axial slots allow for easier deformation of the axial arms during assembly of the second locker to the housing.

Possibly, the axial slots have an opened distal end and a closed opposite proximal end which is proximally located with regard to the adjacent window so that the window is overhanging at a distal end of the second locker. Preferably, the window is totally overhanging at the distal end of the second locker.

Possibly, the axial securing means further include a distal stop of the second locker abutting against a proximal stop of the housing for blocking distal movement of the second locker with respect to the housing. The proximal stop of the housing may be formed by a proximal end of the housing. The distal stop of the second locker may be defined by an outward flange that separates a distal portion of the second locker configured to extend inside the housing and a proximal portion configured to extend outside the housing. The circumferential arm, the axial arms, the axial slots, the window are provided on said distal portion of the second locker.

In an embodiment, the distal abutment surface of the second locker is arranged at a distal end of an axial rib that inwardly protrudes from a lateral wall of said second locker. The axial rib increases the resistance of the second locker to the force applied by the first locker on said second locker. Thus, the resistance to drop tests is improved.

In an embodiment, the axial rib intersects with the window of the second locker. The axial rib is preferably at least located on the circumferential arm of the second locker. More specifically, the axial rib may include a proximal portion extending above (proximal to) the window and a distal portion extending below (distal to) the window, i.e. on the circumferential arm of the second locker.

In an embodiment, the first locker includes a lateral abutment surface configured for abutting against a crest of the axial rib of the second locker to prevent inner deformation of the circumferential arm when the proximal abutment surface of the first locker presses against the distal abutment surface of the second locker. The proximal abutment surface and the lateral abutment surface of the first locker are thus perpendicular and intersect with each other.

In an alternative embodiment, the axial rib is offset the window of the second locker. They are separated by a circumferential gap. The molding of the second locker is accordingly easier. The axial rib may extend alongside the axial slot. The distal end of said axial rib, and so the distal abutment surface of the second locker, may be located between the proximal end and the distal end of said axial slot, or at the level of the window, i.e. proximal to the circumferential arm.

In an embodiment, the first locker includes a stiffener providing support to a proximal shouder that defines the proximal abutment surface of the first locker. The stiffener may be in the form of an axial rib outwardly protruding from an annular ring or a driving leg of the first locker. The stiffener has a proximal end and an opposite distal end, one of them intersecting with one end or with an intermediate portion of proximal shoulder.

Possibly, the first locker includes an annular ring and driving legs separated by a radial flange, and the proximal abutment surface of the first locker is located at said radial flange or below (distal to) said radial flange.

Possibly, the proximal abutment surface of the first locker in the locking position and the distal abutment surface of the second locker in the locking position are separated by an axial gap.

Possibly, the axial rib has a distally decreasing width.

In an embodiment, the autoinjector includes maintaining means for maintaining the second locker in the locking position before use of the autoinjector by the end user.

In an embodiment, the maintaining means include an axial rib arranged on the housing for abutting against an axial arm of the second locker when the second locker is rotated from the blocking towards the release position.

In an embodiment, the maintaining means include an axial rib arranged on the second locker for abutting against an axial rib of the retainer. The axial rib of the housing is here away from the axial arm of the second locker so that there is no friction between this axial rib of the housing and the second locker during movement of the second locker towards the release position.

In an embodiment, the second locker includes an orthoradial pushing surface for allowing a user to apply a torque on the second locker so that the second locker can rotate from the locking position to the release position, the orthoradial pushing surface being arranged on an indicator configured to cooperate with an indicator provided on an outer surface of the housing for indicating the position of the second locker to a user. The indicator of the second locker may be an axially extending rib that protrudes from an outer surface of a lateral wall of the second locker. The axially extending rib is arranged on the proximal portion of the second locker so as to be easily accessible to the user. The orthoradial pushing surface of the axially extending rib makes it easier for the user to overcome the resistance of the maintaining means.

The retainer, the first locker, the second locker and/or the housing (top body) may be symmetrical with regard to the central longitudinal axis A.

BRIEF DESCRIPTION OF THE DRAWINGS

The terms Fig., Figs., Figure, and Figures are used interchangeably in the specification to refer to the corresponding figures in the drawings.

The invention and the advantages arising therefrom will clearly emerge from the detailed description that is given below with reference to the appended drawings as follows.

DESCRIPTION OF THE INVENTION

The different features of the embodiments can be used in combination with and used with other embodiments as long as the combined parts are not inconsistent with or interfere with the operation of the device and assembly. The phraseology and terminology used herein is for the purpose of description and should not be regarded as limiting. The use of "including," "comprising," or "having" and variations thereof herein is to encompass the items listed thereafter and equivalents thereof as well as additional items. Unless limited otherwise, the terms “connected,” “coupled,” and “mounted,” and variations thereof herein are used broadly and encompass direct and indirect connections, couplings, and mountings. In addition, the terms “connected” and “coupled” and variations thereof are not limited to physical or mechanical connections or couplings. As used herein, the singular forms “a,” “an,” and “the” are intended to include the plural forms as well, unless the context clearly indicates otherwise. As used herein, the term “and/or” includes any and all combinations of one or more of the associated listed items. It will be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the scope of the present disclosure.

Figure 1:
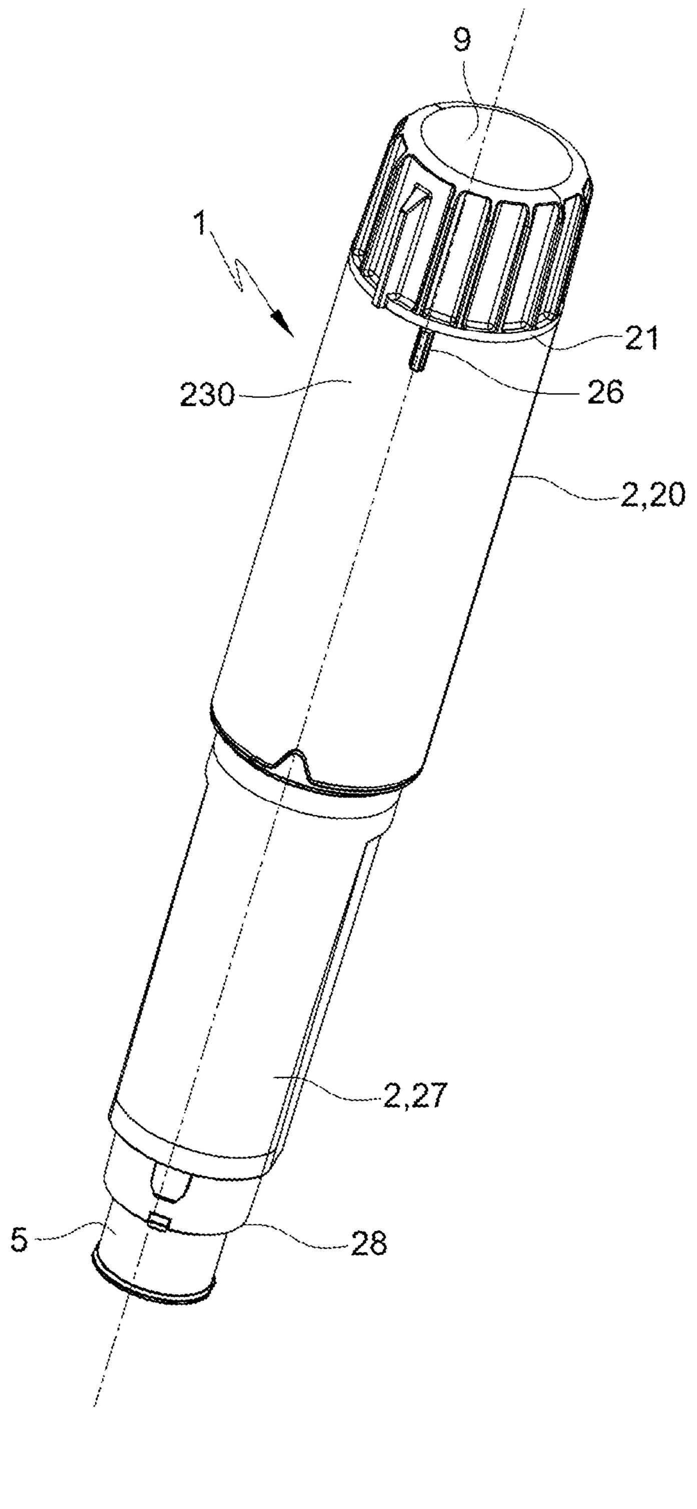
FIG. 1 is a perspective view of an autoinjector according to an embodiment of the invention.
Figure 8:
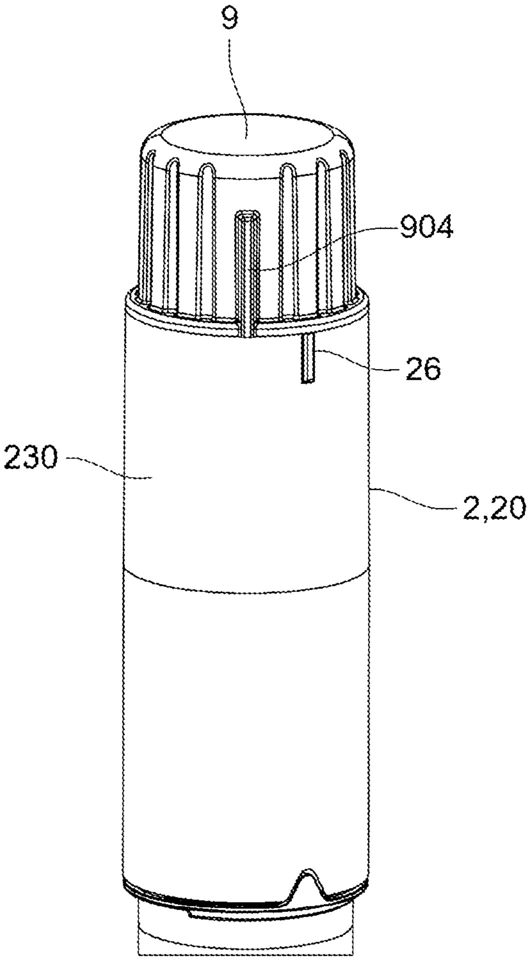
FIG. 8 is a perspective view of an autoinjector according to an embodiment of the invention, the second locker being in a locking position.

With reference to FIG. 1 is shown an autoinjector 1 according to an embodiment of the invention. The autoinjector 1 is designed for automatic injection of a product into an injection site. The autoinjector 1 extends along a longitudinal axis A. The autoinjector 1 includes a housing 2 comprising a top body 20 and a bottom body 27 assembled to each other by any appropriate securing means such as, for instance, snap-fitting means. The top body 20 and the bottom body 27 are axially and rotationally fixed with one another. The housing 2 has a proximal end 21, which is a proximal end 21 of the top body 20, and an opposite distal end 28, which is a distal end 28 of the bottom body 27. A cap (not shown) is removably attached to the distal end of the housing 2. The top body 20 has a cylindrical lateral wall 23 which is opened at the proximal end 21. The proximal end 21 of the housing 2 thus defines a proximal opening 22. The proximal opening 22 may be closed by a top cap which may serve as a second locker 9 as will be explained below. The top body 20 of the housing 2 may include one or two diametrically opposite indicators 26, see FIGS. 8-9, for example in the form of axial ribs, arranged at an outer surface 230 of the lateral wall 23 of the housing 2 for indicating the position of the second locker 9 to a user.

Figure 2:
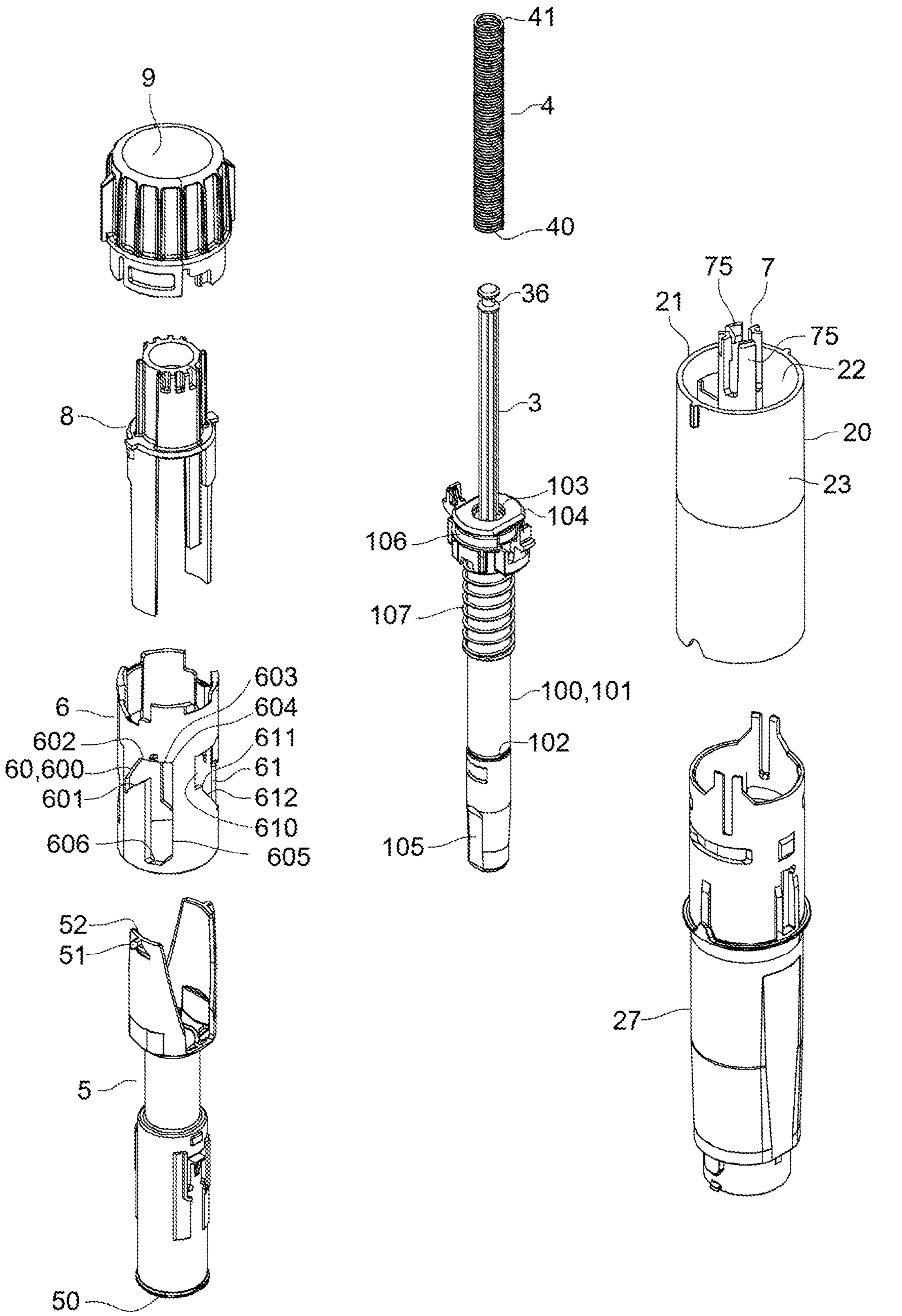
FIG. 2 is an exploded view of an autoinjector according to an embodiment of the invention.
Figure 10A:
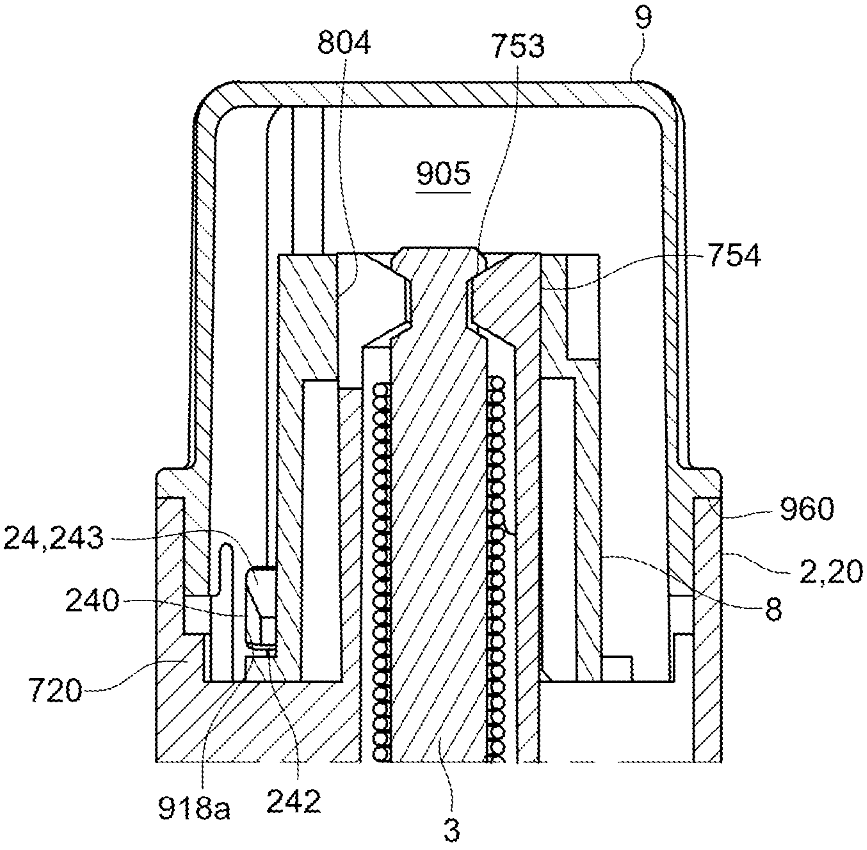
FIG. 10A is a cross-section view of an autoinjector according to an embodiment of the invention, the first locker being in a locking position.
Figure 10B:
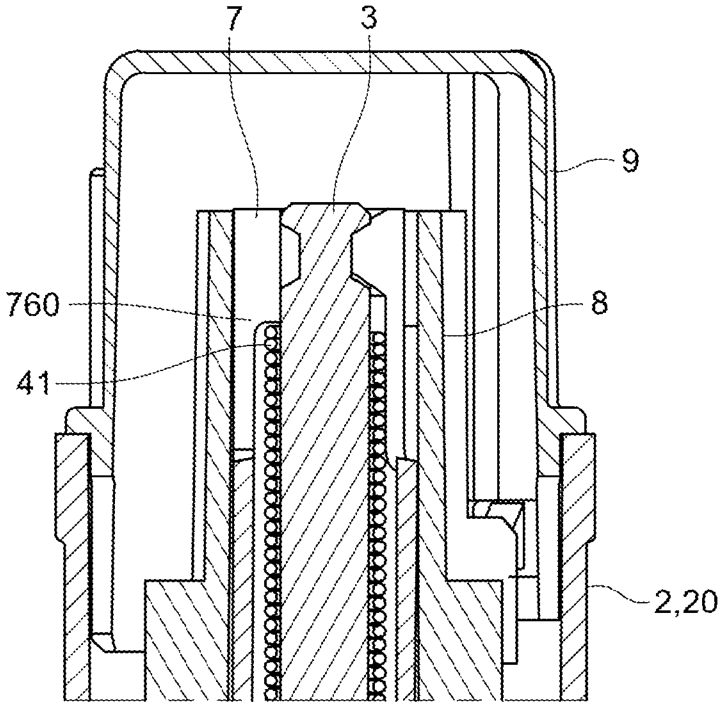
FIG. 10B is a cross-section of the autoinjector of FIG. 10A, in a plane orthogonal to the plane of FIG. 10A.
Figure 10C:
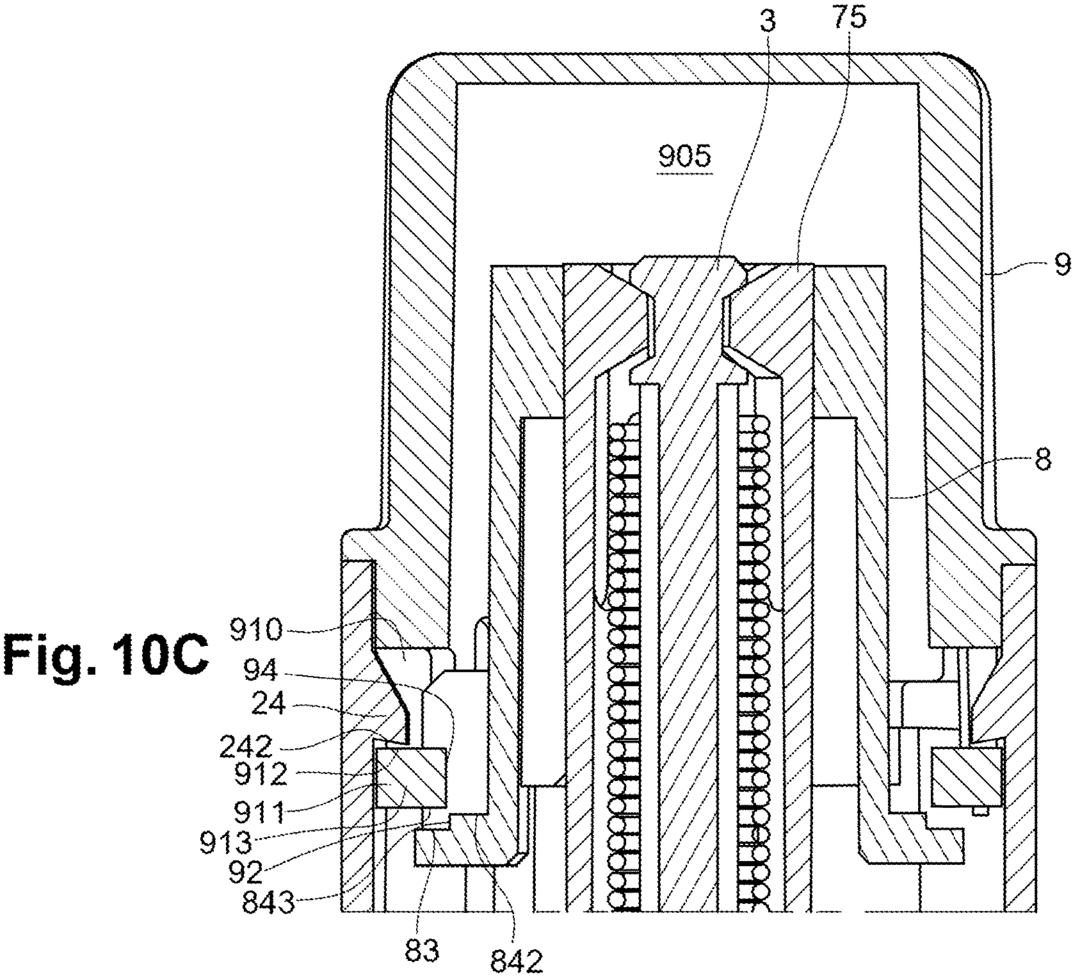
FIG. 10C is another cross-section view the autoinjector of FIG. 10A, the first locker being in a locking position and the second locker being in a locking position.

FIG. 2 illustrates an exploded view of the autoinjector 1. The bottom body 27 is configured to receive a medical container 100, such as a syringe. For instance, the medical container 100 may be a prefilled syringe. The medical container 100 has a tubular barrel 101 defining a reservoir for containing a medical product to be injected. The barrel 101 has a distal end 102 provided with an injection needle (not shown), and a needle shield 105 removably attached to said distal end for protecting and sealing the injection needle. The barrel 101 has an opened proximal end 103 which may be provided with a flange 104 and which is configured to receive a plunger rod 3 urged in the distal direction by biasing means which may be in the form of an injection spring 4. The injection spring 4 has a distal end 40 abutting against (a radial flange 30 of) the plunger rod 3 and a proximal end 41 abutting against a distal shoulder 760 of a retainer 7, FIG. 10B. A ring 106 may be secured to the proximal end 103 of the barrel 101 and may serve as a support for a safety spring 107 configured for pushing a needle cover 5 in the distal direction. As visible on FIG. 2, the autoinjector 1 may also include a rotative cam 6, an axially movable first locker 8 and a rotative second locker 9 which here forms the top cap.

Figure 3:
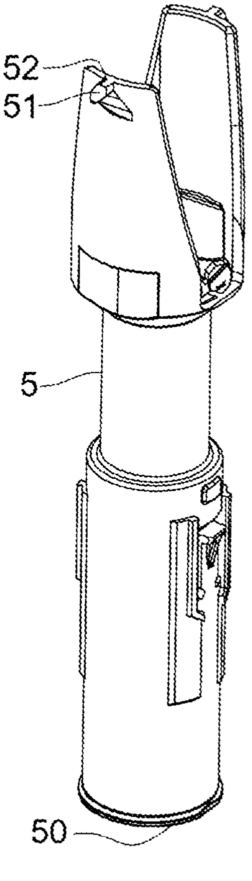
FIG. 3 is a perspective view of a needle cover of an autoinjector according to an embodiment of the invention.

FIG. 3 illustrates the needle cover 5. The needle cover 5 is axially movable along the longitudinal axis A with respect to the housing 2 between a first extended position (pre-use position, not shown), in which the needle cover 5 at least partially or completely shields the injection needle, a retracted position (not shown), proximally located relative to said first extended position, in which the needle cover 5 activates the autoinjector 1 and thus triggers the injection (by pushing the first locker 8 in a release position as will be described below), and a second extended position (safety position, not shown) in which the needle cover 5 moves back in the distal direction to safely shield the injection needle. Movement of the needle cover 5 from the first extended position to the retracted position is caused by the user pressing the distal end of the needle cover 5 against the injection site, and movement of the needle cover 5 from the retracted position to the safety position is due to the safety spring 107 pushing the needle cover 5 back in the distal direction when the user removes the injection needle from the injection site.

The needle cover 5 has a distal end 50 designed to be pressed against an injection site, such as a user’s skin, a radial tab 51 for engaging a first slot 60 of the cam 6, and a proximal pushing surface 52 for abutting against the first locker 8, as will explained in further details below. The contact between the needle cover 5 and the first locker 8 may be direct, i.e. without any intervening parts. The proximal pushing surface 52 may extend in a circumferential direction, but may also include a top surface of the tabs which accordingly define a radial portion of said proximal pushing surface 52 for ensuring abutment between the needle cover 5 and the first locker 8. The proximal pushing surface 52 may be the proximal-most surface of the needle cover 5. The radial tab 51 of the needle cover 5 may engage a rotative cam 6.

With reference to FIG. 2, the cam 6 may be in the form of a cylindrical ring provided with a first slot 60 and a second slot 61. The first slot 60 has an oblique portion 600 extending between a first end 601 and a second end 602, a transversal portion 603 extending from the second end 602 to a third end 604, and an axial portion 605 distally extending from the third end 604 to a fourth end 606. The first slot 60 is engaged by the radial tab 51 of the needle cover 5, said radial tab 51 being located at the first end 601 when the needle cover 5 is in the first extended position, at the second end 602 and at the third end 604 when the needle cover 5 is in the retracted position, and close to or at the fourth end 606 when the needle cover 5 is in the safety position. The second slot 61 includes an axial portion 610 including a proximal shoulder 611, and an oblique portion 612 distally extending from said proximal shoulder 611. The second slot 61 is engaged by the ring 106, which extends in the axial portion 610 when the needle cover 5 is in the first extended position. The cam 6 is pivotally mounted inside the housing 2. Rotation of the cam 6 is first caused by the radial tab 51 sliding against the oblique portion 600 when the needle cover 5 moves from the first extended position to the retracted position, then by the ring 106 sliding against the oblique portion 612 when the ring 106 is pushed distally together with the medical container 100 by the injection spring 4. This second rotation of the cam 6 causes the radial tab 51 to move from the second end 602 to the third end 604, so that the radial tab 51 is then allowed to slide in the axial portion 605 when the needle cover 5 moves from the retracted position to the safety position.

Figure 4:
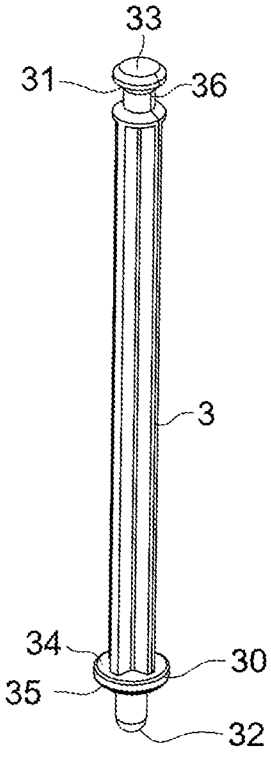
FIG. 4 is a perspective view of a plunger rod of an autoinjector according to an embodiment of the invention.

FIG. 4 illustrates the plunger rod 3. The plunger rod 3 is configured to push a stopper (not shown) arranged inside the barrel 101, to expel the medical product. The plunger rod 3 includes a distal abutment surface 31. The plunger rod 3 is axially movable inside the housing 2 between a storage position (FIGS. 10A-10C, 11, 12 for instance) and an injection end position (not shown) distally located relative to the storage position. In the injection end position, the plunger rod 3 may press the stopper against the distal end of the reservoir formed by the barrel 101. Movement of the plunger rod 3 from the storage position to the injection end position is caused by the biasing means (the injection spring 4) pushing said plunger rod 3 in the distal direction. In the illustrated embodiment, the injection spring 4 extends around the plunger rod 3, so that the plunger rod 3 is inside the injection spring 4. In another embodiment (not shown), the plunger rod 3 may define an inner cavity for receiving the injection spring 4: the plunger rod 3 thus extends around the injection spring 4 and the injection spring 4 is accordingly arranged inside the plunger rod 3.

The plunger rod 3 has a distal end 32 for engaging the stopper and an opposite proximal end 33 which may be configured for cooperating with the retainer 7. The radial flange 30 of the plunger rod 3 may be arranged at the distal end 32 of said plunger rod 3 so that a proximal side 34 of said radial flange 30 may provide support to the distal end 40 of the injection spring 4 and an opposite distal side 35 of said radial flange 30 may abut against the stopper. The proximal end 33 of the plunger rod 3 may include a groove 36 for receiving the retainer 7, such that the retainer 7 can block the plunger rod 3 in the storage position before activation of the autoinjector 1. The groove 36 may be delimited by the distal abutment surface 31 which is configured for abutting against the retainer 7 in the storage position. The distal abutment surface 31 is arranged at the proximal end 33 of the plunger rod 3, and may have a frustoconical shape so that the distal abutment surface 31 is inclined with regards to the longitudinal axis A.

Figure 5A:
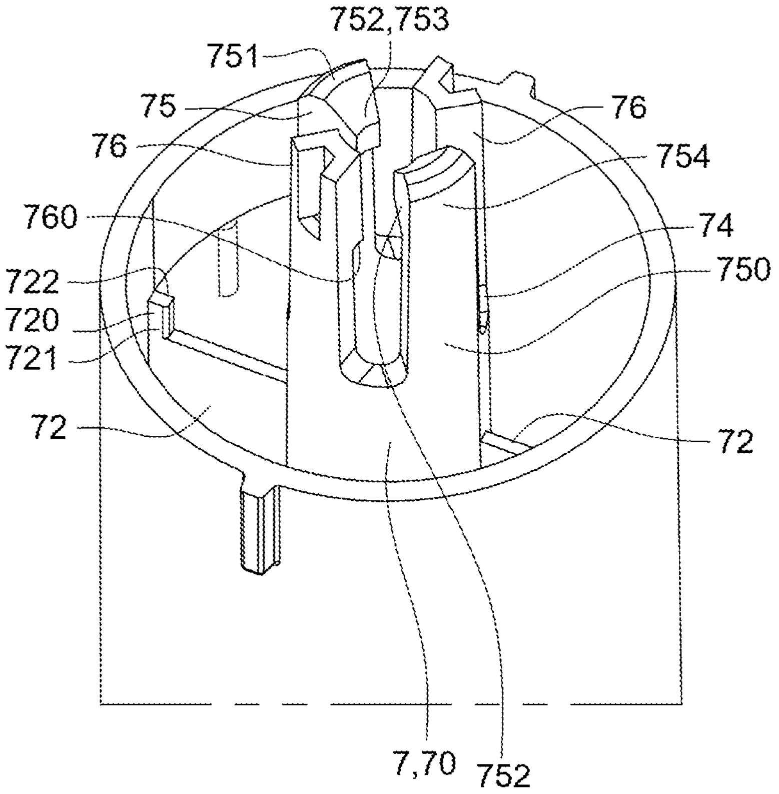
FIG. 5A is a perspective view of a top body of a housing of an autoinjector according to an embodiment of the invention.
Figure 5B:
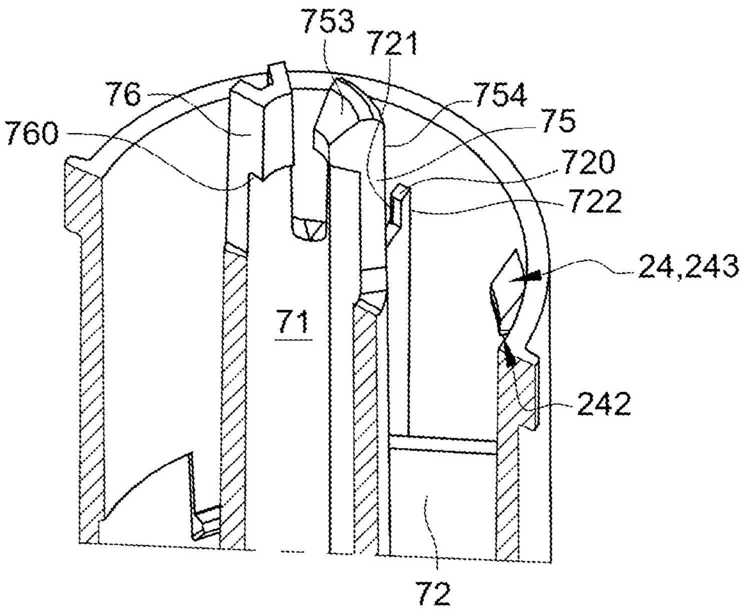
FIG. 5B is a cross-sectioned perspective view of a top body of a housing of an autoinjector according to an embodiment of the invention.

FIGS. 5A and 5B illustrate the retainer 7. The retainer 7 is secured to the top body 20 and extends around the plunger rod 3 to retain the plunger rod 3 in the storage position before activation of the autoinjector 1. The retainer 7 may be in the form of an axial sleeve having a lateral wall 70 defining an inner cavity 71 for receiving the plunger rod 3 and the biasing means. The retainer 7 has connectors 72 for fixedly securing the retainer 7 to the housing 2. The connectors 72 may in the form of radially extending plates that connect an outer surface of the lateral wall 70 of the retainer 7 to an inner surface of the lateral wall 23 of the housing 2. The retainer 7 and the top body 20 are preferably made of a single piece. The retainer 7 has an opened distal end allowing passage of the plunger rod 3 from the storage position to the injection end position and an opposite proximal end 74 provided with one or more blocking members in the form of deformable legs 75 and one or more supporting legs 76 each separated from another by axial slots. For instance, the retainer 7 includes two diametrically opposite deformable legs 75 and two diametrically opposite supporting legs 76, although their number may vary. The supporting legs 76 define a distal shoulder 760 that supports the proximal end 41 of the biasing means (injection spring 4).

The deformable legs 75 are outwardly radially deformable between a blocking position (see for instance FIGS. 10A, 10B), in which they axially block the plunger rod 3 in the storage position, and a release position (not shown), in which they allow for axial movement of the plunger rod 3 from the storage position to the injection end position. Movement of the deformable legs 75 from the locking position to the release position is caused by the injection spring 4 pressing the plunger rod 3 against said deformable legs 75.

The deformable legs 75 extend along the longitudinal axis A, and include a distal end 750 secured to the lateral wall 70 of the retainer 7 and an opposite proximal end 751 provided with a inner radial protrusion 752 which is configured to engage the groove 36 of the plunger rod 3. The inner radial protrusion 752 defines a proximal abutment surface 753 for axially abutting against the distal abutment surface 31 of the plunger rod 3. The proximal abutment surface 753 may have a frustoconical shape and may thus be inclined with regard to the longitudinal axis A, so as to ease outward movement of the deformable legs 75 under the action of the injection spring 4. The proximal abutment surface 753 of the deformable legs 75 and the distal abutment surface 31 of the plunger rod 3 may be complementarily shaped. In the blocking position, the proximal abutment surface 753 of the deformable legs 75 axially abuts against the distal abutment surface 31 of the plunger rod 3. In the release position, the proximal abutment surface 753 of the deformable legs 75 is radially shifted away the distal abutment surface 31 of the plunger rod 3 such that the plunger rod 3 can move towards the injection end position. Radially opposite the inner radial protrusion 752, the deformable legs 75 may define a lateral abutment surface 754 configured for radially abutting the first locker 8. The first locker 8 thus prevents movement of the deformable legs 75 from the blocking position to the release position.

Still with reference to FIGS. 5A-5B, the housing 2 includes a lug 24 that protrudes from the inner surface of the lateral wall 23 of said housing 2. The lug 24 is aimed at axially securing the second locker 9 to the top body 20. The lug 24 defines a distal stop 242 for axially abutting against the second locker 9 and a proximal ramp portion 243 for allowing insertion of the second locker 9 inside the housing 2. The housing 2 may further include an axial rib 25 that protrudes from the inner surface of the lateral wall 23. The axial rib 25 may have a rounded or cylindrical shape.

Figure 6A:
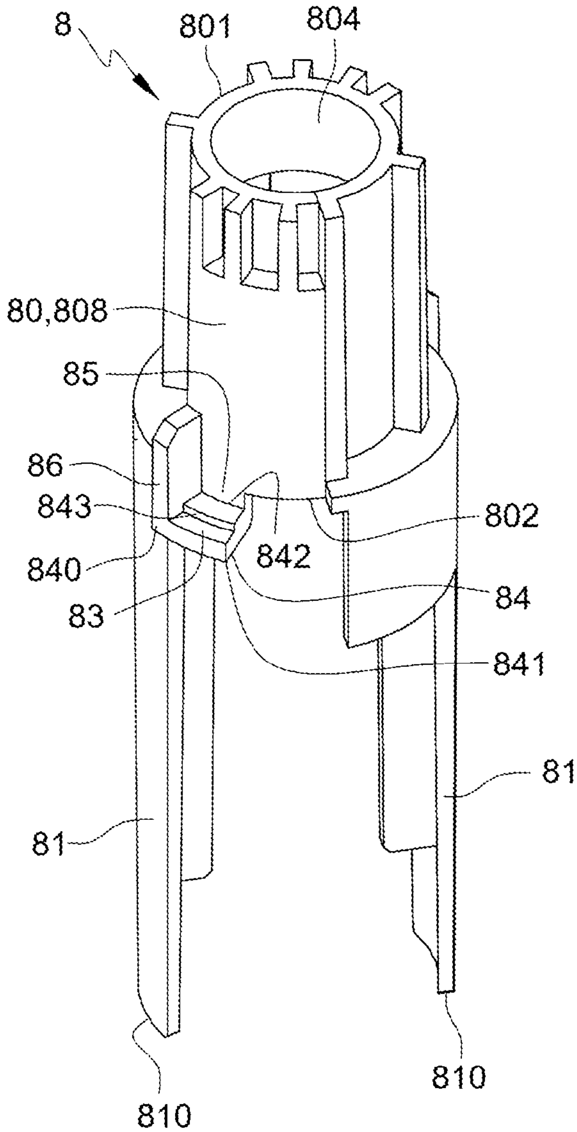
FIG. 6A is a perspective view of a first locker of an autoinjector according to an embodiment of the invention.
Figure 6B:
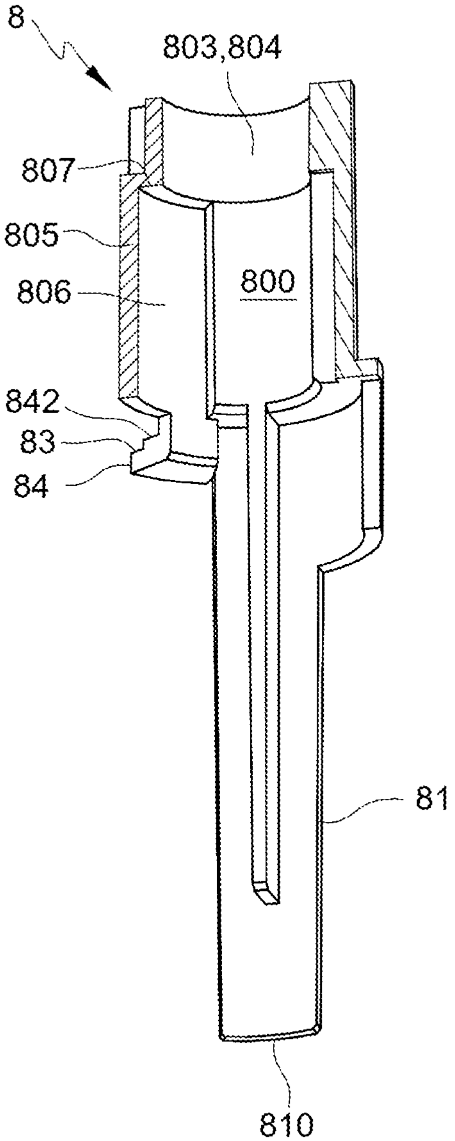
FIG. 6B is a cross-sectioned perspective view of a first locker of an autoinjector according to an embodiment of the invention.

FIGS. 6A and 6B illustrate the first locker 8. The first locker 8 extends around the retainer 7 and is configured for preventing or allowing movement of the retainer 7 from the blocking position to the release position. To that end, the first locker 8 is coupled to and axially movable with respect to the housing 2 between a blocking position, FIG. 10A, in which the first locker 8 prevents deformation of the deformable legs 75 of the retainer 7 towards the release position, and a release position, FIG. 12, proximally located with respect to the locking position, in which the first locker 8 allows for deformation of said deformable legs 75 towards their release position. Movement of the first locker 8 between the blocking position and the release position is caused by the needle cover 5 pushing the first locker 8 in the proximal direction when the needle cover 5 moves from the first extended position to the retracted position. It is contemplated that the autoinjector 1 may be devoid of any obstacle, such as hard points or protrusions, that would hinder movement of the first locker 8 towards the release position (and that would accordingly increase the activation force). The activation force may here only depend on the force of the safety spring 107 that pushes the needle cover 5 in the distal direction.

The first locker 8 may include an annular ring 80 defining an inner cavity 800 for receiving the retainer 7. The inner cavity 800 has an opened proximal end 801 and an opened distal end 802. The annular ring 80 includes a proximal portion 803 and a distal portion 805 separated by a distal shoulder 807. The distal portion 805 has a greater inner diameter than the proximal portion 803. The proximal portion 803 defines an inner lateral abutment surface 804 for radially abutting against the deformable legs 75 of the retainer 7 when the first locker 8 is in the blocking position. The lateral abutment surface 804 of the first locker 8 and the lateral abutment surface 754 of the retainer 7 may be complementarily shaped. The distal portion 805 includes inner axial grooves 806 configured for receiving the deformable legs 75 of the retainer 7 when the first locker 8 is in the release position. The axial grooves 806 thus allow for outward deformation of the deformable legs 75, which can move to their release position under the action of the injection spring 4. In the release position of the first locker 8, the lateral abutment surface 804 of the first locker 8 no longer abuts against the lateral abutment surface 754 of the deformable legs 75 so that nothing prevents the retainer 7 to move to the release position.

The first locker 8 includes axially extending driving legs 81 arranged at the distal end 802 of the annular ring 80 for axially abutting against the needle cover 5, such that movement of said needle cover 5 towards the retracted position causes movement of the first locker 8 towards the release position. The driving legs 81 may distally protrude from a radial flange 82 that outwardly radially protrudes from the annular ring 80. The driving legs 81 include a distal pushing surface 810, which may be provided at a distal end of the driving legs 81, for axially abutting against the proximal pushing surface 52 of the needle cover 5. The distal pushing surface 810 longitudinally extends in a circumferential direction. The distal pushing surface 810 may be the distal-most surface of the first locker 8.

The first locker 8 further includes a proximal abutment surface 83 for axially abutting against the second locker 9, thereby preventing axial movement of the first locker 8 from the blocking position to the release position, as long as the second locker 9 is in a blocking position. The proximal abutment surface 83 may be defined by a proximal shoulder 84 that outwardly radially protrudes from an outer surface 808 of the annular ring 80. The proximal shoulder 84 may be connected to the annular ring 80 by an axial extension 85, such that the proximal abutment surface 83 may be distally located with respect to the distal end 802 of the annular ring 80 or to the radial flange 82. A stiffener 86, in the form of an axial rib, may proximally or distally protrude from the proximal shoulder 84 to increase the resistance of the proximal shoulder 84 to axial forces. The stiffener 86 may be located at one end 840 of the proximal shoulder 84. The opposite end 841 of the proximal shoulder 84 is free of any orthoradial obstacle to allow for movement of the second locker 9 towards the release position. The proximal shoulder 84 may further include a proximal step 842 that defines a lateral abutment surface 843.

Figure 7:
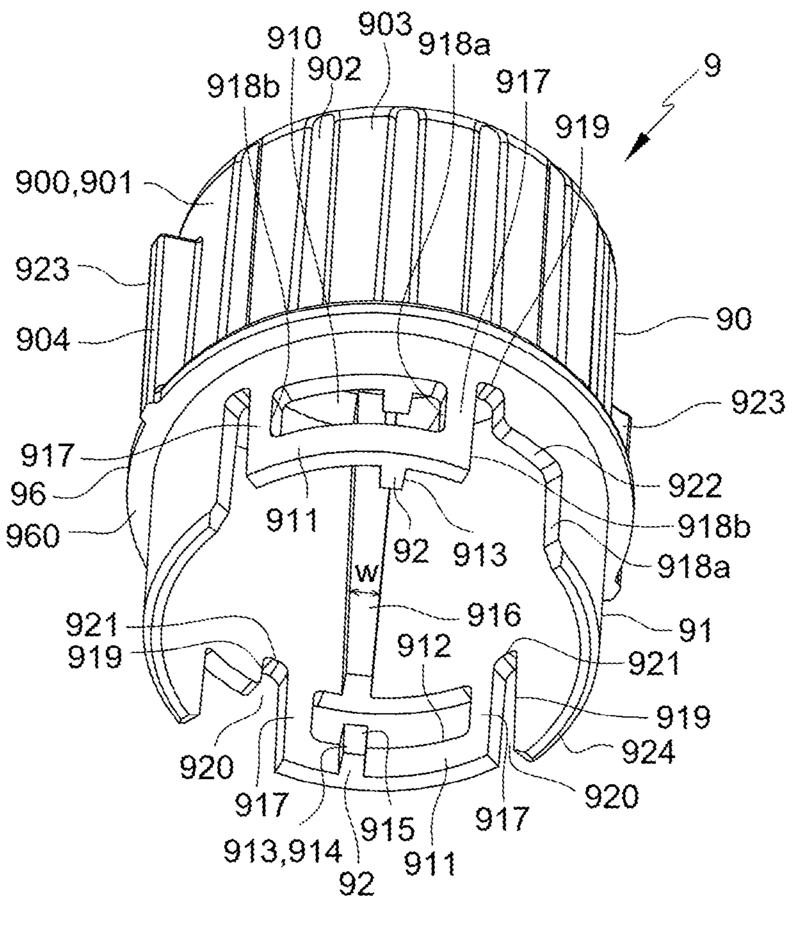
FIG. 7 is a perspective view of a second locker of an autoinjector according to an embodiment of the invention.

FIG. 7 illustrate the second locker 9. The second locker 9 is arranged at the proximal end 21 of the housing 2 for preventing or allowing axial movement of the first locker 8 from the blocking position to the release position. The second locker 9 is coupled to and rotationally movable with respect to the top body 20 between a blocking position, see for instance FIGS. 8 and 10C-10D, in which the second locker 9 prevents the first locker 8 from leaving the blocking position, and a release position, see FIGS. 9 and 11-12, in which the second locker 9 allows for axial movement of the first locker 8 from the blocking position to the release position. Movement of the second locker 9 from the blocking position to the release position is caused by the user grasping the second locker 9 and applying torque to said second locker 9 in order to use the autoinjector 1.

The second locker 9 may include a distal portion 91 and a proximal portion 90 separated by an outward flange 96. The distal portion 91 is configured to extend within the top body 20, while the proximal portion is configured to extend outside the top body 20. The proximal portion 90 has a lateral wall 900 defining an inner cavity 905 configured for receiving the first locker 8 and providing room for the first locker 8 so that the first locker 8 can move in the proximal direction until the release position. The lateral wall 900 has an outer surface 901 provided with alternated axial grooves 902 and axial protrusions 903 for improving the user's grasp on the second locker 9. The outer surface 901 may further include one or two diametrically opposite indicators 904, for example in the form of axial ribs, for indicating the position of the second locker 9 to the user. When the second locker 9 is in the blocking position (FIG. 8), the indicator 904 of the second locker 9 and the indicator 26 of the housing 2 may be offset; when the second locker 9 is in the release position (FIG. 9), they may be axially aligned. The indicators 904 of the second locker 9 may define an orthoradial pushing surface 923 that helps apply a torque to the second locker 9. The outward flange 96 defines a distal stop 960 that axially abuts against the proximal end 21 of the housing 2 to stop insertion of the second locker 9 within the housing 2.

Figure 12:
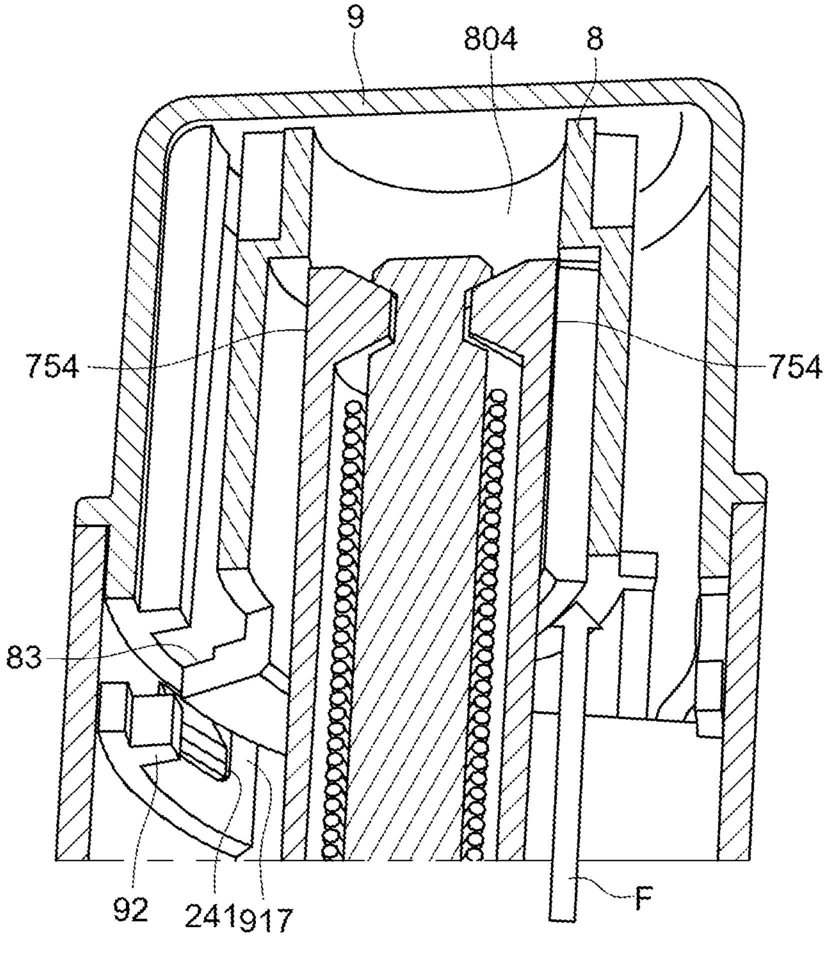
FIG. 12 is a cross-sectioned perspective view of an autoinjector according to an embodiment of the invention, the second locker being in the release position and the first locker being in a release position.

The distal portion 91 includes securing means for axially securing the second locker 9 to the housing 2, while allowing rotation of the second locker 9 with respect to said housing 2. As illustrated in FIGS. 7 and 12, the securing means may include a window 910 configured for engaging the lug 24 of the housing 2. The window 910 is delimited by a circumferential arm 911 and two axial arms 917. The circumferential arm 911 defines a proximal stop 912 configured for axially abutting against the distal stop 242 of the lug 24. The circumferential arm 911 and the axial arms 917 may be resiliently deformable to allow the second locker 9 to pass over the lug 24. The circumferential arm 911 and the two axial arms 917 thus form snap-fitting means.

The circumferential arm 911 further includes an axial rib 913, that inwardly protrudes from an inner surface of the circumferential arm 911, said axial rib 913 defining a distal abutment surface 92 for axially abutting against the first locker 8. In the blocking position of the second locker 9, the distal abutment surface 92 axially faces or abuts against the proximal abutment surface 83 of the first locker 8. Thus, the distal abutment surface 92 of the second locker 9 prevents movement of the first locker 8 from the blocking position to the release position. The proximal force that may be applied by the first locker 8 to the second locker 9 (for instance during a drop test), is transmitted to the housing 2 by means of the axial abutment between the circumferential arm 911 of the second locker 9 and the distal stop 242 of the lug 24. This reliably prevents inadvertent activation of the autoinjector 1. Besides, to avoid inward deformation of the circumferential arm 911 (and thus disassembly of the second locker 9 and the housing 2), the axial rib 913 may have a crest 914 configured for radially abutting against the lateral abutment surface 843 of the step 842 of the first locker 8. In the release position of the second locker 9 (FIG. 11), the distal abutment surface 92 is offset the proximal abutment surface 83 of the first locker 8 so that the first locker 8 can move to the release position (FIG. 12). With reference to FIG. 7, the axial rib 913 may have a distal portion 915, that may define the distal abutment surface 92, and a proximal portion 916, axially separated from each other by the window 910. The axial rib may have a proximally increasing width w.

Figure 10D:
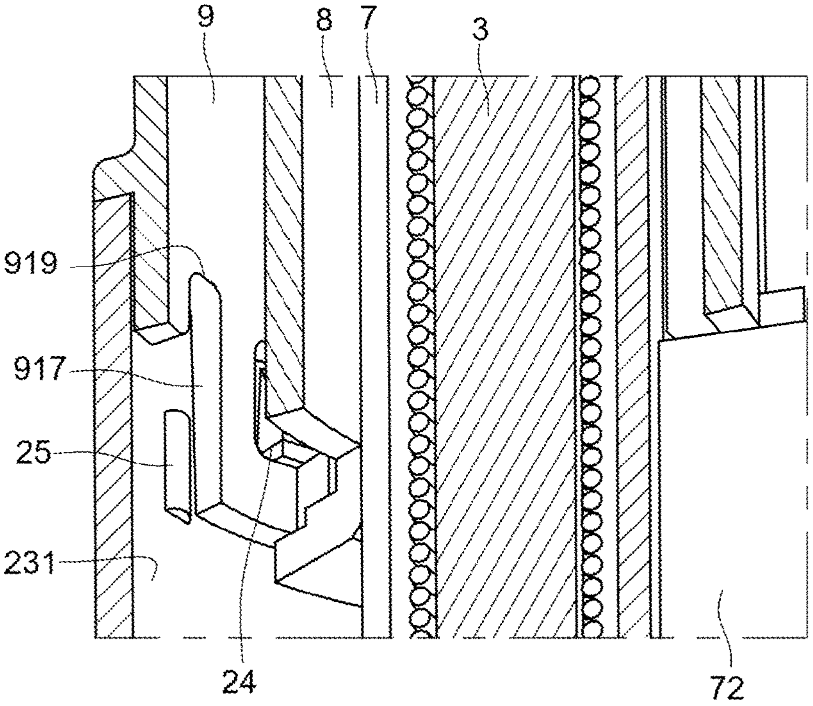
FIG. 10D is a perspective view of a detail of FIG. 10C.

Blocking means may be provided for limiting rotation of the second locker 9 relative to the housing 2 to a predetermined angle. The blocking means preferably include the two axial arms 917. The two axial arms 917 may indeed define orthoradial stops 918*a*, 918*b*, configured for abutting, respectively, against one side 240 and against the other side 241 of the lug 24. FIG. 10D illustrates the second locker 9 in the blocking position; a first one of the two axial arms 917*a* abuts against a first side 240 of the lug 24 for blocking rotation of the second locker 9 in a first direction. FIG. 12 illustrates the second locker 9 in the release position; a second one of the two axial arms 917*b* abuts against a second side 241 of the lug 24 for blocking rotation of the second locker 9 in a second direction opposite the first direction. Alternatively or complementarily, FIG. 5A, the blocking means may include an axial rib 720 proximally protruding from a connector 72, said axial rib 720 including a first side 721 for abutting against a first orthoradial stop 918*a* (which may delimit the notch 922) when the second locker 9 is in the blocking position so that the second locker 9 is blocked in the first direction, and an opposite second side 722 for abutting against a second orthoradial stop 918*b* formed by one side of an axial arm 917 (which may delimit the notch 922) when the second locker 9 is in the release position so that the second locker 9 is blocked in the second direction.

With reference to FIG. 7, the second locker 9 (its distal portion) may include axial slots 919 extending on both sides of the window 910. The axial slots 919 may have an opened distal end 920 and an opposite closed proximal end 921, which is preferably arranged proximal to the two axial arms 917 and the window 910. The axial slots 919 ease deformation of the window 910. The second locker 9 may also include a notch 922.

With reference to FIG. 10D, the autoinjector 1 may further include maintaining means for selectively preventing or allowing rotation of the second locker 9 from the blocking position to the release position. The maintaining means may include an axial rib 25, that may protrude from an inner surface 231 of the lateral wall 23 of the housing 2, configured for abutting against the first one of the two axial arms 917 when the second locker 9 is in the blocking position. The axial rib 25 may be shaped to block rotation of the second locker 9 in the second direction (towards the release position) when the torque applied to the second locker 9 is lower than a predetermined threshold, and to allow for rotation of the second locker 9 in the second direction when the torque applied to the second locker 9 by the user is equal to or higher than a predetermined threshold. This prevents inadvertent rotation of the second locker 9 from the blocking position to the release position. The axial rib 25 may have a cylindrical shape to ease deformation of the axial arm 917 and the circumferential arm 911 so that they can pass over the axial rib 25 when the user rotates the second locker 9 towards the release position.

The operation of the autoinjector 1 illustrated in FIGS. 8-12 is described below.

Initially (FIGS. 8, 10A-10D), the second locker 9 and the first locker 8 are in the blocking position, so that the autoinjector 1 cannot be activated, even during a drop test or any other accidental fall. The distal abutment surface 92 of the second locker 9 axially faces the proximal abutment surface 83 of the first locker 8 and the proximal stop of the second locker 9 abuts against the distal stop 242 of the housing 2. Thus, the first locker 8 cannot leave the blocking position. The lateral abutment surface 804 of the first locker 8 accordingly maintains the deformable legs 75 in their locking position, so that the plunger rod 3 cannot move towards the injection end position despite the action of the injection spring 4.

Figure 9:
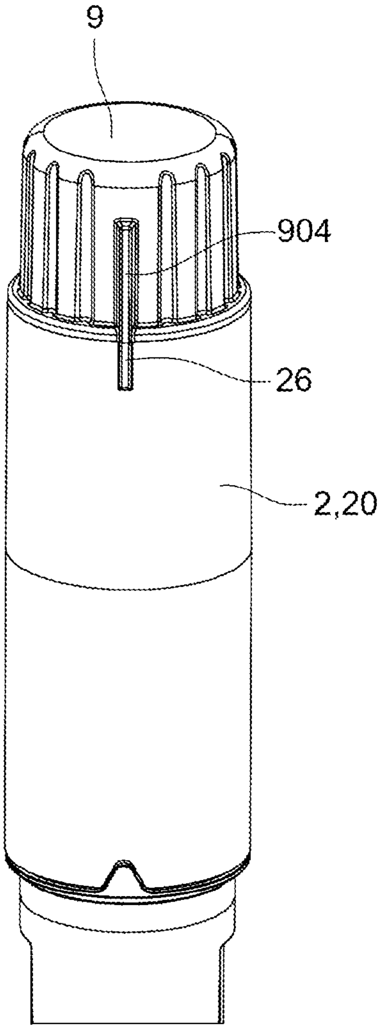
FIG. 9 is a perspective view of an autoinjector according to an embodiment of the invention, the locker being in a release position.
Figure 11:
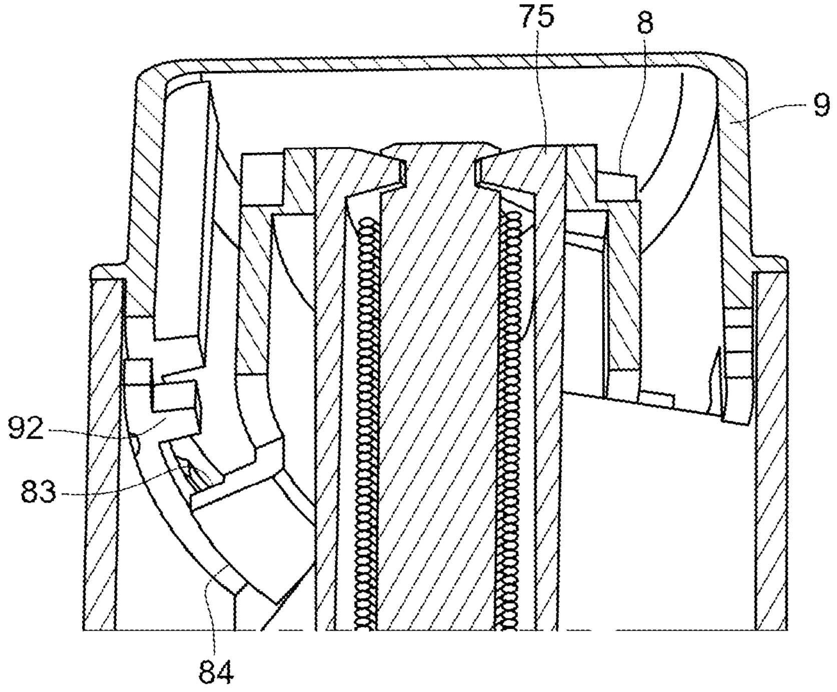
FIG. 11 is a cross-sectioned perspective view of an autoinjector according to an embodiment of the invention, the second locker being in the release position and the first locker being in a locking position.

In order to perform injection, the user has to remove the cap (not shown) from the bottom body 27 to unveil the distal end 50 of the needle cover 5 (FIG. 1), and to rotate the second locker 9 so that the second locker 9 reaches the release position (FIG. 9). The first locker 8 is still in the blocking position. However, the distal abutment surface 92 of the second locker 9 is now offset the proximal abutment surface 83 of the first locker 8 (FIG. 11). Thus, the first locker 8 is no longer prevented from moving towards the release position.

The user then presses the distal end 50 of the needle cover 5 against the injection site. As a result, the needle cover 5 moves in the proximal direction from the first extended position towards the retracted position. By doing so, the proximal pushing surface 52 of the needle cover 5 abuts against the driving legs 81 of the first locker 8, so that the needle cover 5 pushes the first locker 8 in the proximal direction too (see FIG. 12, arrow F), until the first locker 8 reaches the release position. Preferably, the first locker 8 does not encounter any obstacle so that the activation force stays as low as possible. At this stage, the deformable legs 75 of the retainer 7 are no longer prevented from moving towards their release position. Due to the action of the injection spring 4, the deformable legs 75 outwardly deform and the plunger rod 3 is pushed in the distal direction. The plunger rod 3 accordingly pushes the medical container in the distal direction so that the injection needle penetrates into the injection site and the plunger rod 3 then engages the stopper in the barrel 101 so that the medical product is expelled into the injection site.

Figure 13A:
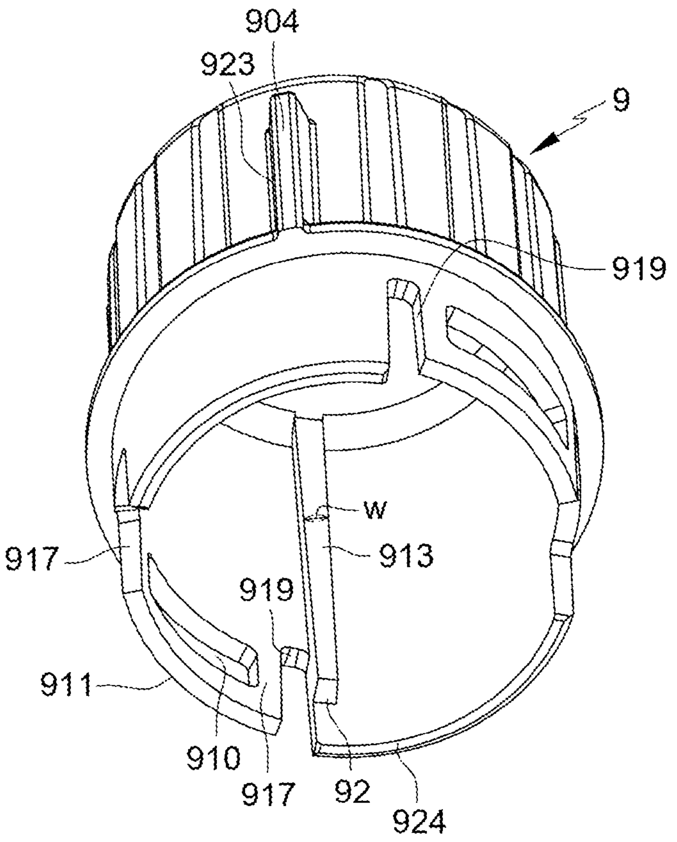
FIGS. 13A and 13B are perspective views of a second locker of an autoinjector according to a second embodiment of the invention.
Figure 13B:
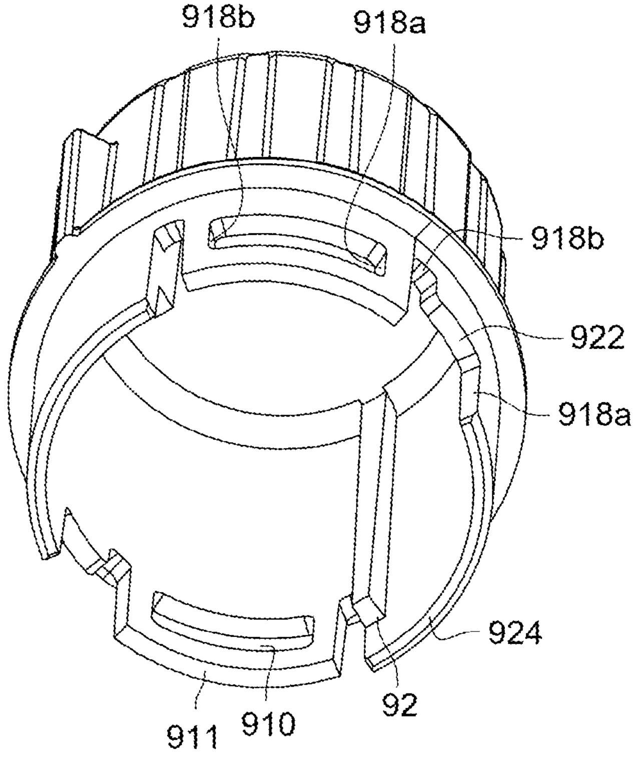

FIGS. 13A-13B illustrate the second locker 9 according to another embodiment. The same numeral references apply to the features which are similar to the above-described embodiments. The second locker 9 of FIGS. 13A-13B differs in that the distal abutment surface 92 is now away from the window 910, i.e. offset from the window 910. The axial rib 913 no longer intersects the window 910. Instead, the axial rib 913 extends alongside one of the axial slots. Besides, the axial rib 913 may include a single continuous portion, instead of a proximal portion and a distal portion separated from each other by the window 910. The distal abutment surface 92 may further be arranged at the level of the window 910, i.e. proximal to the circumferential arm 911 or the distal end 924 of the second locker 9.

Figure 14A:
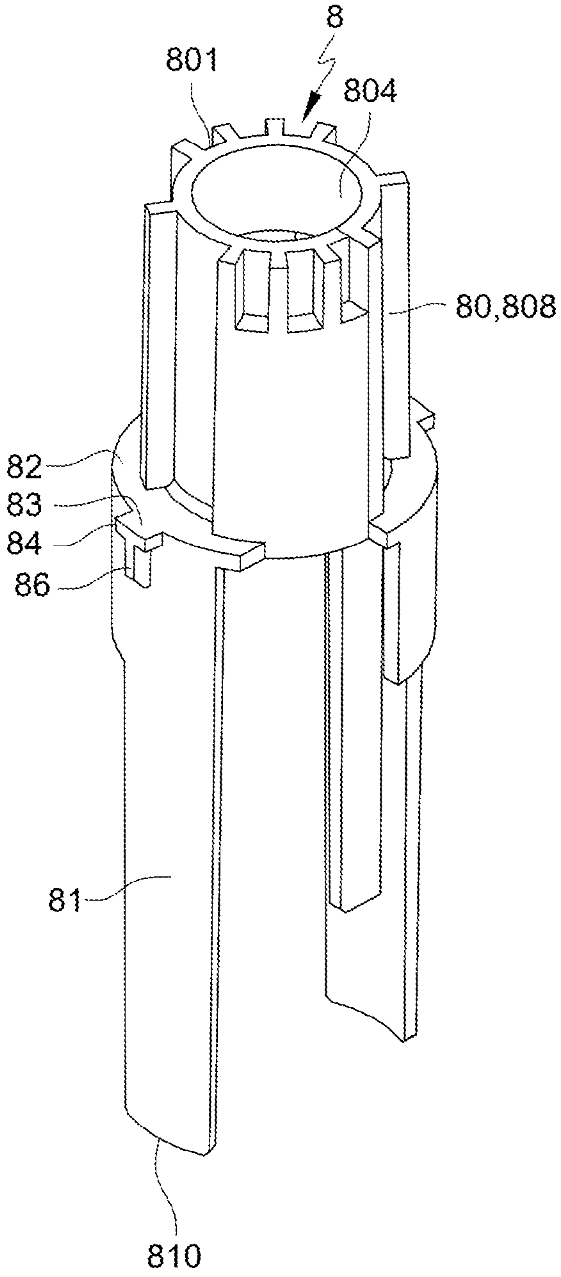
FIGS. 14A and 14B are, respectively, a perspective view and a cross-sectioned perspective view of a first locker of an autoinjector according to a second embodiment of the invention.
Figure 14B:
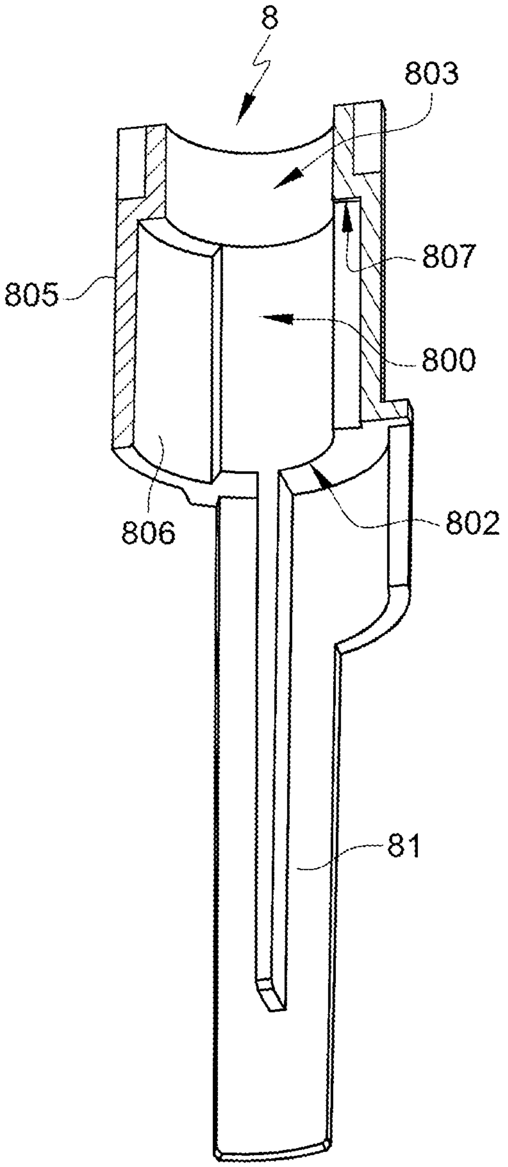
Figure 15:
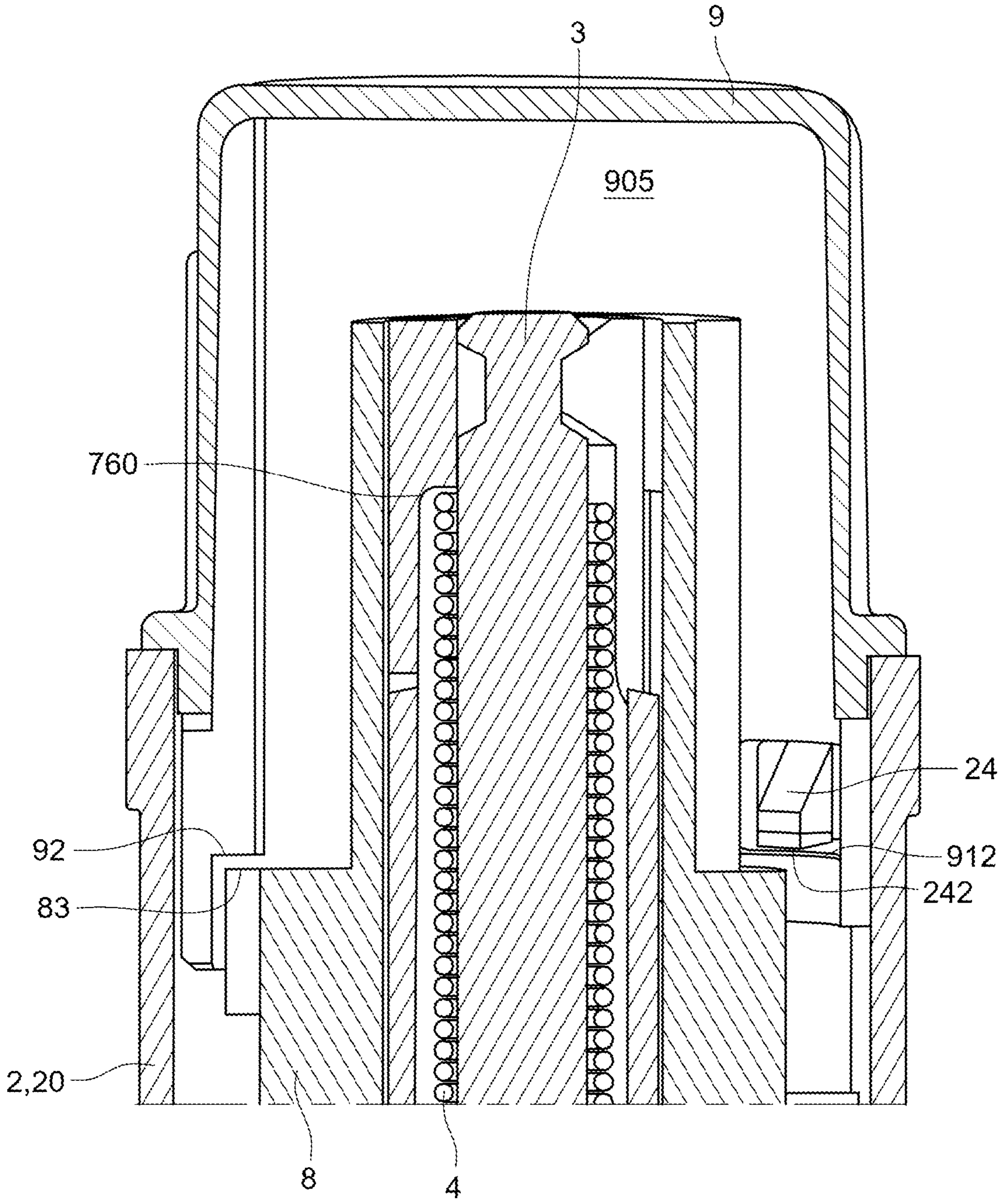
FIG. 15 is a cross-section view of an autoinjector according to a second embodiment of the invention, the first locker being in the locking position and the second locker being in the locking position.
Figure 16:
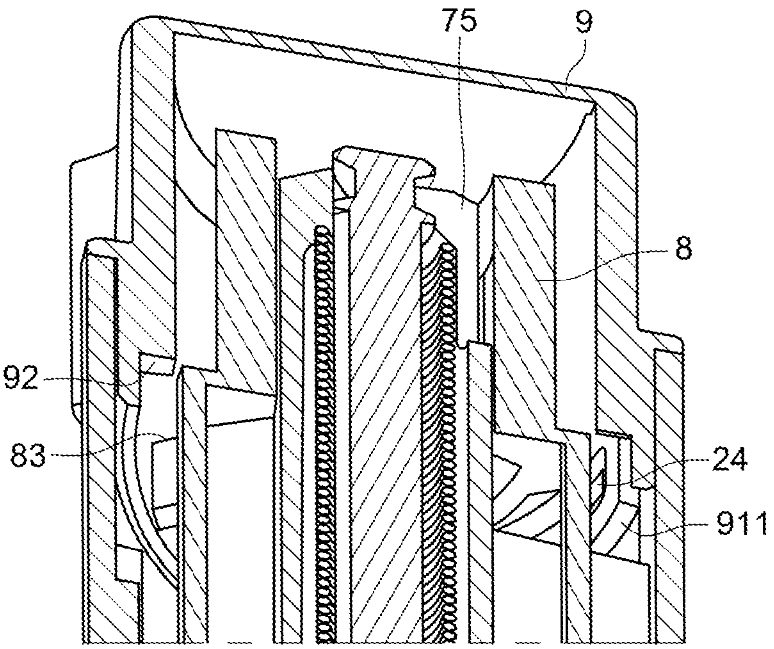
FIG. 16 is a cross-sectioned perspective view of an autoinjector according to a second embodiment of the invention, the first locker being in the locking position and the second locker being in the release position.
Figure 17:
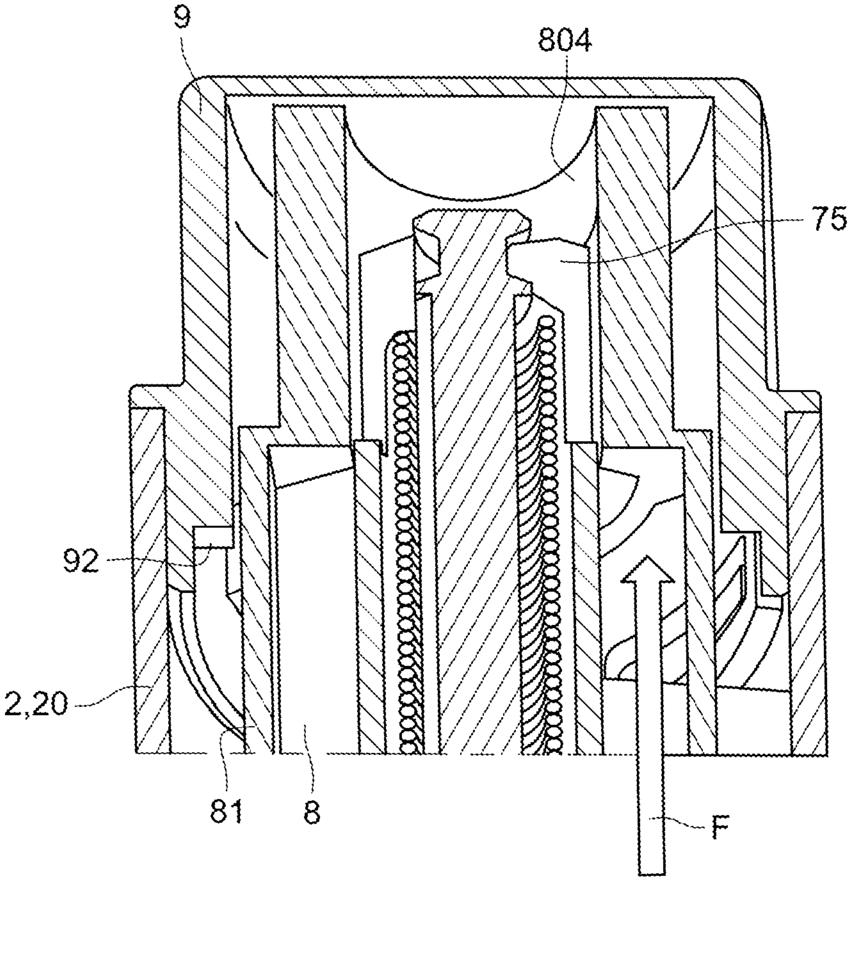
FIG. 17 is a cross-sectioned perspective view of an autoinjector according to a second embodiment of the invention, the first locker being in the release position and the second locker being in the release position.

FIGS. 14A-14B illustrate the first locker 8 configured for cooperating with the second locker 9 of FIGS. 13A-13B. The same numeral references apply to the features which are similar to the above-described embodiments. Instead of protruding from an outer surface 808 of the annular ring 80, the proximal shoulder 84 here protrudes from an outer surface of the driving legs 81 or of the outward flange 96. The first locker 8 is further devoid of the step 842 for radially abutting against the circumferential arm 911. The stiffener 86 distally protrudes from the proximal shoulder 84, and may be located between the two ends of the proximal shoulder 84, i.e. at an intermediate portion of said proximal shoulder 84.

The operation of the first locker 8 and second locker 9 of FIGS. 13A-13B and 14A-14B is similar to the operation of the first locker 8 and second locker 9 of FIGS. 8-12.

Figure 18:
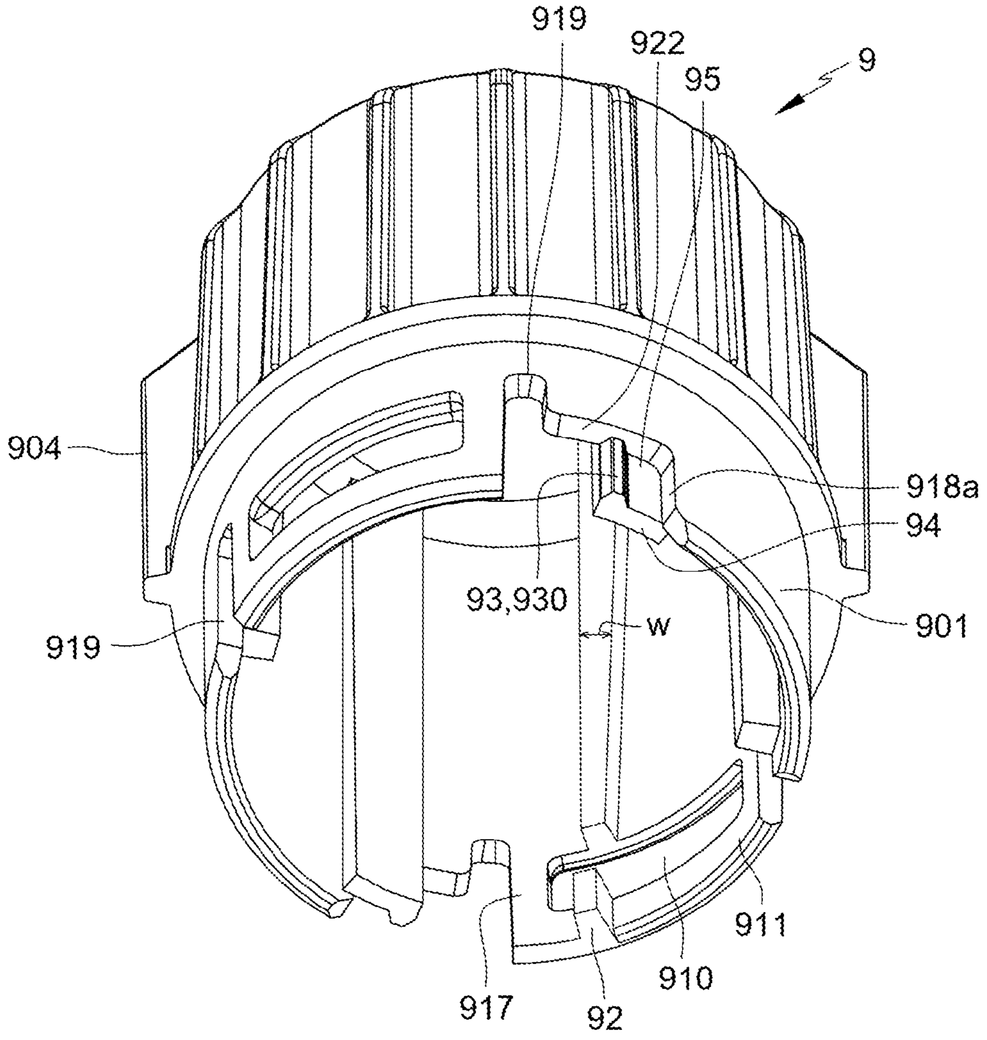
FIG. 18 is a perspective view of a second locker of an autoinjector according to an embodiment of the invention.
Figure 19A:
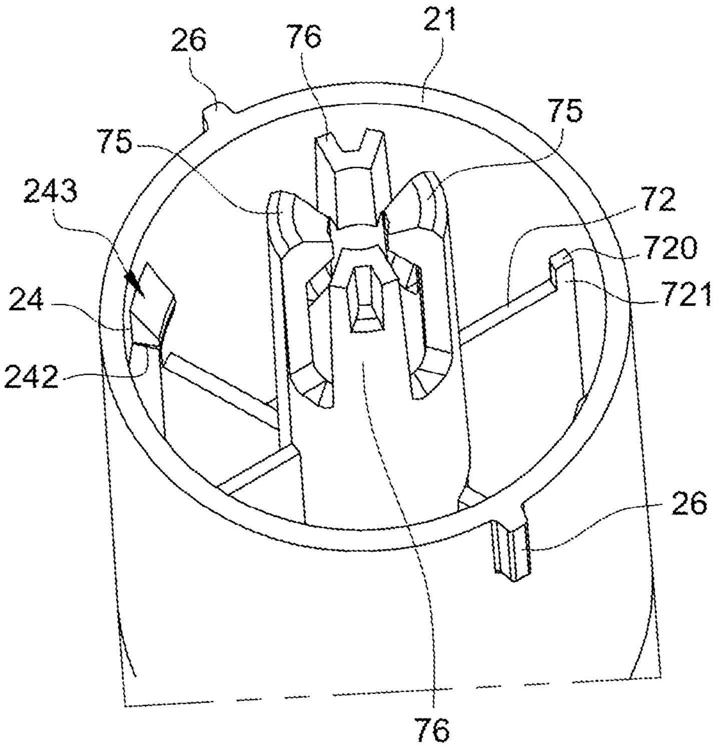
FIGS. 19A and 19B are perspective views of a top body of a housing of an autoinjector according to an embodiment of the invention, for cooperating with the second locker of FIG. 18.
Figure 19B:
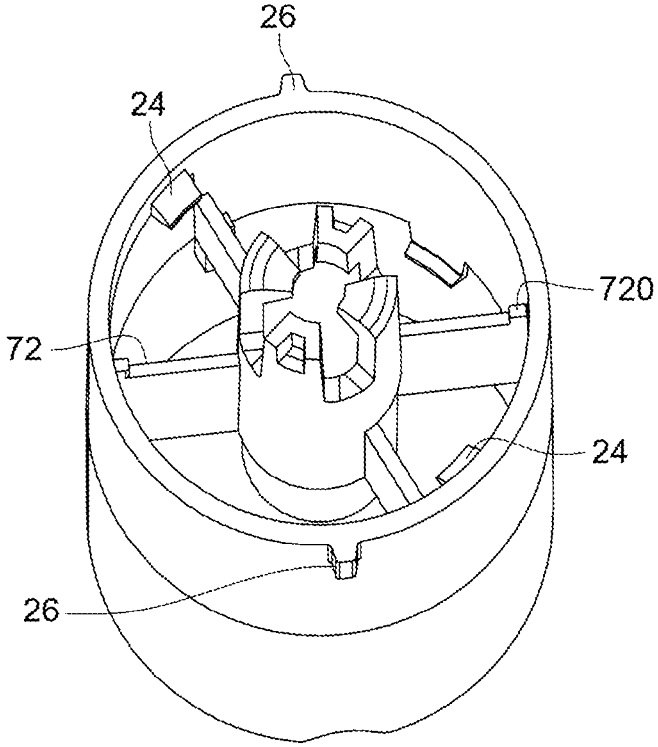

FIGS. 18 and 19A-19B illustrate an alternative version of the maintaining means. The maintaining means include an axial rib 93, but the axial rib 93 is here arranged on the second locker 9 and configured for abutting against the first side 721 of the axial rib 720 of the connector 72, when the second locker 9 is in the blocking position. The axial rib 93 may be shaped to block rotation of the second locker 9 in the second direction (towards the release position) when the torque applied to the second locker 9 is lower than a predetermined threshold, and to allow for rotation of the second locker 9 in the second direction when the torque applied to the second locker 9 by the user is equal to or higher than a predetermined threshold. This prevents inadvertent rotation of the second locker 9 from the blocking position to the release position. The axial rib 93 may have a cylindrical shape to ease passage over the axial rib 720 of the connector 72 when the user rotates the second locker 9 towards the release position. The axial rib 93 may be located in the notch 922, and may specifically protrude from an axial wall 94 that is recessed with regards to the outer surface 901 of the second locker 9, such that a radial gap exists between a crest 930 of said axial rib 93 and an inner surface of the lateral wall 23 of the housing 2. This also eases passage of the axial rib 93 over the retainer 7. The recess 95 defined between the first orthoradial stop and the axial rib 93 is configured for receiving the corresponding axial rib 720 of the retainer 7. As visible in FIGS. 19A-19B, the housing 2 may be devoid of the axial rib 25 so that any friction between this axial rib 25 and the circumferential arm 911 is deleted during rotation of the second locker 9 from the blocking position to the release position.

It is readily understandable from the above description that the autoinjector 1 of the invention permits to reduce the activation force while still reliably preventing inadvertent activation of the autoinjector 1.

It is to be understood that the present invention is not limited to the embodiments described above and illustrated in the drawings; rather, the skilled person will recognize that many changes and modifications may be made within the scope of the appended claims.

The invention claimed is:

1. An autoinjector, for automatic injection of a medical product into an injection site, said autoinjector comprising:

a housing extending along a longitudinal axis A and configured to receive a medical container having a barrel defining a reservoir for containing the medical product, said barrel having a distal end provided with an injection needle and an opened proximal end configured to receive a plunger rod for pushing a stopper arranged inside the barrel, a needle cover coupled to and axially movable with respect to said housing between a first extended position, in which the needle cover at least partially shields the injection needle, a retracted position, in which the needle cover moves proximally with respect to the housing, and a second extended position in which the needle cover moves back in a distal direction to shield the injection needle, the plunger rod axially movable inside the housing between a storage position and an injection end position distally located relative to the storage position, the plunger rod being configured to push the stopper in order to expel the medical product when moving from the storage position to the injection end position, biasing means for biasing the plunger rod in the distal direction towards the injection end position, a retainer for maintaining the plunger rod in an initial position against the action of the biasing means, the retainer including a blocking member radially movable between a blocking position, in which the blocking member axially abuts against a distal abutment surface of the plunger rod for blocking the plunger rod in the initial position, and a release position, in which the blocking member is away from the distal abutment surface of the plunger rod to allow for movement of the plunger rod in the distal direction, a first locker, axially movable with respect to the retainer between a locking position, in which a lateral abutment surface of the first locker radially abuts against the blocking member to maintain the blocking member in the blocking position, and a release position, in which the lateral abutment surface of the first locker is axially shifted away from the blocking member, axial movement of the first locker from the locking position to the release position being caused by the needle cover moving from the first extended position to the retracted position, a second locker, rotationally movable around the longitudinal axis A with respect to said housing, between a locking position in which a distal abutment surface of the second locker is configured for axially abutting against a proximal abutment surface of the first locker, thereby preventing axial movement of the first locker from the locking position to the release position, and a release position in which the distal abutment surface of the second locker is shifted away from the proximal abutment surface of the first locker, thereby allowing axial movement of the first locker from the locking position to the release position, axial securing means for axially securing the second locker with respect to the housing.

2. The autoinjector according to claim 1, wherein the second locker is arranged at a proximal end of the housing and defines an inner cavity configured for receiving the first locker when the first locker moves from the locking position to the release position.

3. The autoinjector according to claim 1, wherein the biasing means have a proximal end abutting against a distal shoulder of the retainer and an opposite distal end abutting against the plunger rod, and the blocking member includes an inner radial protrusion for engaging a groove of the plunger rod, the inner radial protrusion being arranged proximal to the distal shoulder of the retainer.

4. The autoinjector according to claim 1, wherein the axial securing means include a distal stop arranged on the housing for abutting against a proximal stop of the second locker.

5. The autoinjector according to claim 4, wherein the proximal stop is provided on a radially inwardly deformable circumferential arm of the second locker, and the distal stop is provided on a lug of the housing.

6. The autoinjector according to claim 5, wherein the second locker further includes two axial arms for connecting the circumferential arm to the second locker, the two axial arms and the circumferential arm defining a window configured for receiving the lug.

7. The autoinjector according to claim 1, wherein the distal abutment surface of the second locker is arranged at a distal end of an axial rib that inwardly protrudes from a lateral wall of said second locker.

8. The autoinjector according to claim 7, wherein the axial rib intersects with the window of the second locker.

9. The autoinjector according to claim 8, wherein the first locker includes a lateral abutment surface configured for abutting against a crest of the axial rib of the second locker to prevent inner deformation of the circumferential arm when the proximal abutment surface of the first locker presses against the distal abutment surface of the second locker.

10. The autoinjector according to claim 7, wherein the axial rib is offset the window of the second locker.

11. The autoinjector according to claim 1, wherein the first locker includes a stiffener providing support to a proximal shoulder that defines the proximal abutment surface of the first locker.

12. The autoinjector according to claim 1, wherein the autoinjector includes maintaining means for maintaining the second locker in the locking position before use of the autoinjector by the end user.

13. The autoinjector according to claim 12, wherein the maintaining means include an axial rib arranged on the housing for abutting against an axial arm of the second locker when the second locker is rotated from the blocking towards the release position.

14. The autoinjector according to claim 12, wherein the maintaining means include an axial rib arranged on the second locker for abutting against an axial rib of the retainer.

15. The autoinjector according to claim 1, wherein the second locker includes an orthoradial pushing surface for allowing a user to apply a torque on the second locker so that the second locker can rotate from the locking position to the release position, the orthoradial pushing surface being arranged on an indicator configured to cooperate with an indicator provided on an outer surface of the housing for indicating the position of the second locker to a user.

* * * * *